US00PP07784P

United States Patent [19]

Meilland

[11] Patent Number: Plant 7,784

[45] Date of Patent: Feb. 11, 1992

[54] ROSE PLANT—MEICIJAS VARIETY

[75] Inventor: Alain A. Meilland, Antibes, France

[73] Assignee: The Conard-Pyle Company, West Grove, Pa.

[21] Appl. No.: 580,252

[22] Filed: Sep. 10, 1990

[51] Int. Cl.[5] ..... A01H 5/00

[52] U.S. Cl. ..... Plt./15

[58] Field of Search ..... Plt./11, 15

[56] References Cited

U.S. PATENT DOCUMENTS

P.P. 5,622 1/1986 Meilland ..... Plt. 11

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly forms very double long lasting blossoms which are an attractive light lemon yellow in coloration. With the exception of its distinctive blossom coloration the characteristics of the new variety are substantially identical to those of its partent Meijason variety (U.S. Plant Pat. No. 5,622). The plant exhibits an upright growth habit, forms vigorous vegetation, and is well suited for service as attractive ornamentation in the landscape. Additionally, the plant is not particularly affected by crypotgamic diseases.

1 Drawing Sheet

SUMMARY OF THE INVENTION

The new variety of the present invention originated as a sport of unknown causation among plants of the Meijason variety (U.S. Plant Pat. No. 5,622) and was discovered during a selective study of such plants. I was attracted to a single plant of the new variety whose flowers while having the same shape and form as its parent exhibited a distinctive and very attractive light lemon yellow coloration instead of the usual blossom coloration of the parent variety. Had I not discovered and preserved this new variety it would have been lost to mankind.

It was found that the new and distinct variety of Hybrid Tea rose plant exhibits the following combination of characteristics:

(a) from the physical point of view the plant has an upright growth habit, forms dark green adult wood and has characteristics very similar to its parent Meijason variety (U.S. Plant Pat. No. 5,622) with the exception that its very double long lasting flowers while having the same shape and form have a distinctive light lemon yellow coloration instead of the very light cream yellow edged with luminous pink coloration of its parent, and (b) from the biological point of view the plant forms vigorous vegetation and is not particularly affected by cryptogamic diseases.

With the exception of the distinctive blossom coloration the characteristics of the new variety are substantially identical to those of the Meijason variety.

The new variety well meets the needs of the horticultural industry and is particularly well suited for use as attractive ornamentation in parks and gardens.

The new variety has been found to undergo asexual propagation by a number of conventional routes, including budding, grafting, and cuttage. Asexual reproduction by the above mentioned methods as performed in France shows that the characteristics of the new variety are strictly transmissible from one generation to another and appears to be firmly fixed.

The new variety has been named the Meicijas variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were three years of age and were observed during April while budded on *Rosa indica* understock and growing in greenhouses at Cap d'Antibes, France.

DETAILED DESCRIPTION

Figures 1, 2, 3, 4, 5, 6, 7, 8, 9, 10, 11, 12, 13, 14, 15:
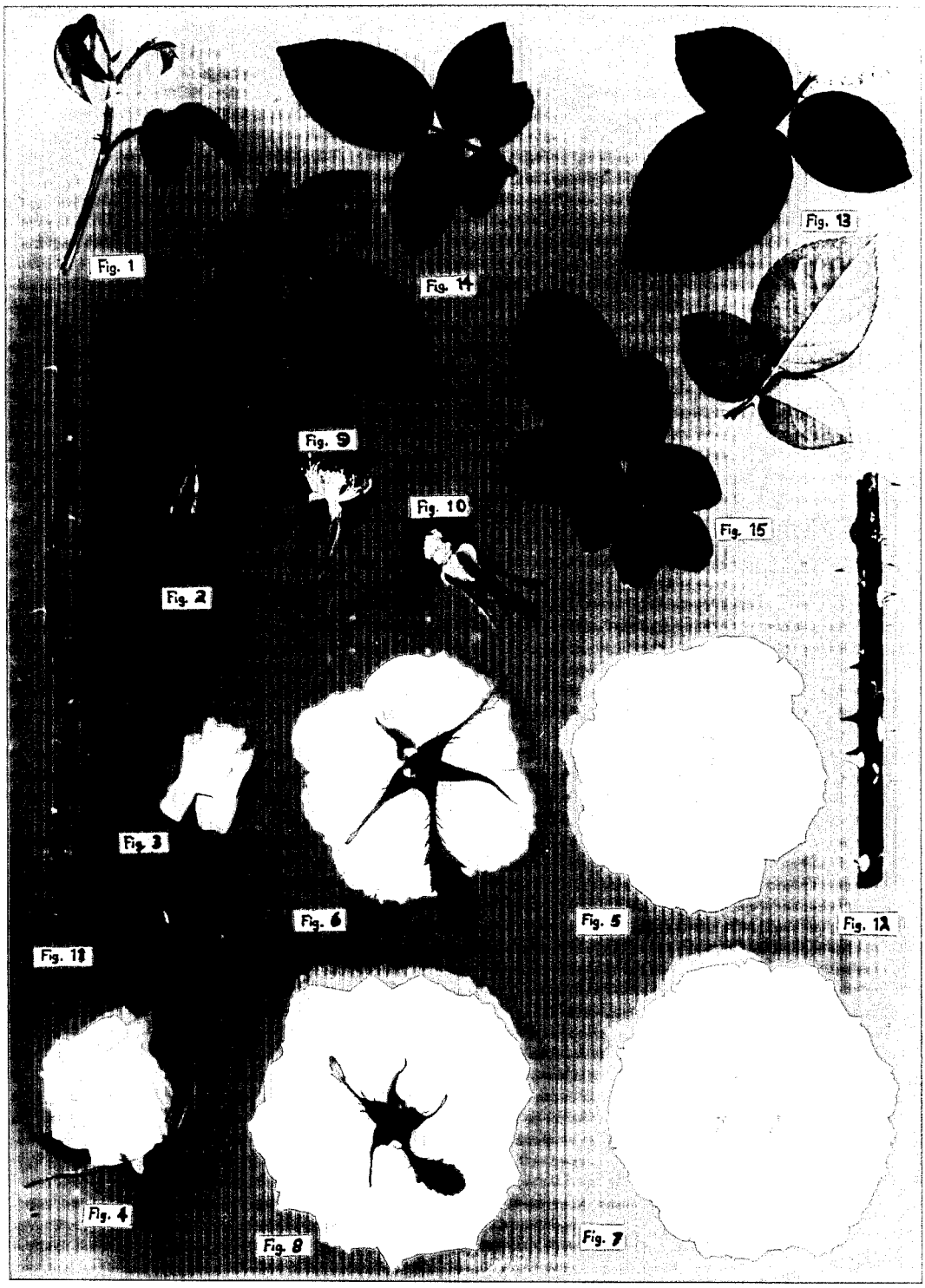
FIG. 1 illustrates a specimen of a young shoot.
FIG. 2 illustrates a specimen of a floral bud at the opening of the sepals.
FIG. 3 illustrates a specimen of a floral bud at the opening of the petals.
FIG. 4 illustrates a specimen of a flower in the course of opening.
FIG. 5 illustrates a specimen of an open flower — plan view — obverse.
FIG. 6 illustrates a specimen of an open flower — plan view — reverse.
FIG. 7 illustrates a specimen of a fully open flower — plan view — obverse.
FIG. 8 illustrates a specimen of a fully open flower — plan view — reverse.
FIG. 9 illustrates a specimen of a floral receptacle showing the arrangement of the stamens and pistils.
FIG. 10 illustrates a specimen of a floral receptacle showing the arrangement of the pistils (stamens removed)
FIG. 11 illustrates a specimen of a flowering stem.
FIG. 12 illustrates a specimen of a main branch.
FIG. 13 illustrates specimens of two leaves with three leaflets — plan view — upper surface (top) and lower surface (bottom)
FIG. 14 illustrates specimens of leaves with five leaflets — plan view — upper surface (top) and lower surface (bottom)
FIG. 15 illustrates a specimen of a leaf with seven leaflets — plan view — upper surface.

The chart used in the identification of the colors is that of the The Royal Horticultural Society (R.H.S. Colour Chart). The description is based on the observation of three year old plants made during April while budded on *Rosa indica* understock and growing in greenhouses at Cap d'Antibes, France. The coloration in common terms precedes reference to the chart.

Class: Hybrid Tea.

Plant:

*Height.*—When the plants are cut back to a height of approximately 85 cm., flowering stems commonly are formed having a length of 40 to 70 cm. When grown in fields in Wasco, Calif., the height of the plant is approximately 100 to 110 cm. at the end of the growing season.

*Habit.*—Upright.

Branches:

*Color.*—Young stems: light green, Yellow-Green Group 146B. Adult Wood: dark green, Yellow-Green Group 147A.

*Thorns.*—Size: medium. Quantity: very numerous, and sometimes mingled with tiny prickles and gladular acicules. Color: pinkish changing to greenish on young stems, and straw changing to tan on mature wood.

Leaves:

*Stipules.*—Adnate, pectinate, fairly wide and linear.

*Petioles.*—Upper surface: striped reddish brown on young foliage and light green more or less stained with reddish coloration on mature foliage with more or less glandular edges. Under surface: light green, bear only a few hooked prickles and sometimes some small glandular acicules.

*Leaflets.*—Number: 3, 5 (most often), and 7. Shape: elliptic, spearlike. Serration: single and regular. Texture: leathery. General appearance: very ample and dense, mat foliage. Color (young foliage): Under surface: light green, Yellow-Green Group 146B, more or less stained with reddish coloration. Upper surface: reddish brown, more or less shaded with greenish coloration on the central vein and at the bottom of the leaflet. Color (adult foliage): Upper surface: dark green, Yellow-Green Group 147A. Under surface: medium green, Yellow-Green Group 147B.

Inflorescence:

*Number of flowers.*—Usually one single bloom per stem. However, sometimes axillary buds below the blooms may develop, especially when forced in greenhouses.

*Peduncle.*—Straight, rigid, bears numerous hooked prickles mingled with glandular acicules. The length is approximately 11 cm. on average.

*Sepals.*—Upper surface: tomentose, greenish in coloration. Under surface: medium green with edges that are more or less glandular, the outer sepals are narrow and have appendiculated edges.

*Buds.*—Shape: conical before the opening of the sepals. Length: approximately 3 cm. on average. Size: medium. Color (upon opening): Upper surface: dark lemon yellow, Yellow-Orange Group 14A. Under Surface: light lemon yellow, Yellow-Orange Group 14C.

*Flower.*—Shape: sides tend to be parallel, fully double. Diameter: approximately 12 cm. on average. Color (when opening begins): Upper surface: light lemon yellow, Yellow-Orange Group 14B. Under Surface: light lemon yellow, Yellow-Orange Group 14C. Color: (when blooming): Upper surface: light lemon yellow, Yellow-Orange Group 14C, and turning more or less white on the outer petals depending on the season. Under Surface: light lemon yellow, Yellow-Orange Group 14C, turning white on the outer petals. Color (at end of opening): Upper surface: light lemon yellow, Yellow-Orange Group 14C, turning white on the outer petals and on the outside of the inner petals more or less strongly depending on the season. Under surface: light lemon yellow, Yellow-Orange Group 14D, turning white on the outer petals and on the outside of the inner petals, more or less strongly depending upon the season. Fragrance: slight. Lasting quality: long when cut and placed in a vase. Petal number: approximately 30 on average. Petal shape: rounded and indented on the top, and wavy at the edge. Texture: consistent. Petal drop: good. Stamen number: approximately 104 on average. Anthers: straw edged with fuschia. Filaments: yellowish and of irregular heights. Pistils: approximately 96 on average. Stigmas: yellow with a hint of ochre. Styles: fuschia at the top, yellowish and tomentose at the base, more or less twisted and of irregular heights. Receptacle: medium green and in longitudinal section it is in the shape of a pitcher.

Development:

*Vegetation.*—Vigorous.

*Blooming.*—Abundant.

*Resistance to Diseases.*—Excellent.

*Aptitude to Greenhouse Forcing.* —Very good.

I claim:

1. A new and distinct variety of Hybrid Tea rose plant characterized by the following combination of characteristics:

(a) from the physical point of view the plant has an upright growth habit, forms dark green adult wood and has characteristics very similar to its parent Meijason variety (U.S. Plant Pat. No. 5,622) with the exception that its very double long lasting flowers while having the same shape and form have a distinctive light lemon yellow coloration instead of the very light cream yellow edged with luminous pink coloration of its parent, and (b) from the biological point of view the plant forms vigorous vegetation and is not particularly affected by cryptogamic diseases;

substantially as herein shown and described.

* * * * *